United States Patent [19]
Tornier

[11] 4,266,302
[45] May 12, 1981

[54] FEMORAL PIN FOR HIP PROSTHESIS

[75] Inventor: Alain Tornier, Le Brocey-Crolles, France

[73] Assignee: Etablissements Tornier, St. Ismier, France

[21] Appl. No.: 81,228

[22] Filed: Oct. 2, 1979

[30] Foreign Application Priority Data

Oct. 11, 1978 [FR] France .................. 78 29594

[51] Int. Cl.³ .................................... A61F 1/03
[52] U.S. Cl. .................................... 3/1.912; 128/92 C
[58] Field of Search ............. 128/92 BC, 92 B, 92 R, 128/92 BA, 92 G, 92 C, 92 CA; 3/1.9, 1.91, 1.911, 1.912, 1.913

[56] References Cited

U.S. PATENT DOCUMENTS

| 3,466,670 | 9/1969 | Christiansen | 3/1.913 |
| 3,848,273 | 11/1974 | Frey | 3/1.913 |
| 3,978,528 | 9/1976 | Crep | 3/1.91 |
| 4,040,130 | 8/1977 | Laure | 3/1.91 |

FOREIGN PATENT DOCUMENTS 923085 2/1955 Fed. Rep. of Germany ...... 128/92 BC

*Primary Examiner*—Clifford D. Crowder
*Attorney, Agent, or Firm*—Dowell & Dowell

[57] ABSTRACT

A femoral pin for a hip prosthesis, wherein the pin is in the form of a plurality of funicular elements, or strands, issuing from a hilt member.

4 Claims, 4 Drawing Figures

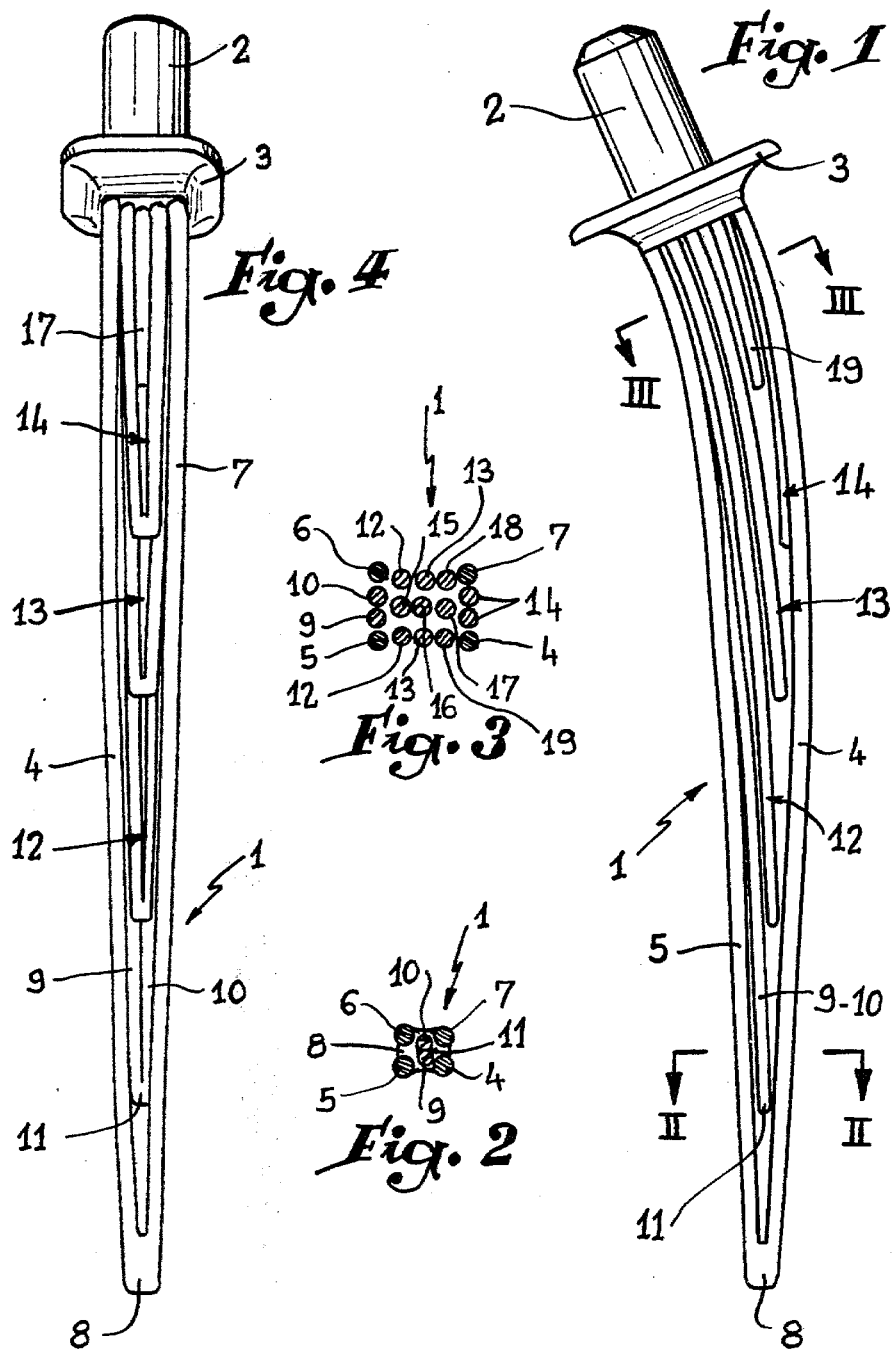

FEMORAL PIN FOR HIP PROSTHESIS

The present invention relates to improvements in prostheses for the hip of the type comprising a femoral pin which is driven into the medullary cavity of the femur and the end of which bears a ball joint adapted to be engaged in the natural or artificial acetabulum of the hip bone.

The femoral pins of known prostheses are rigid, with the result that it is relatively difficult for them to abut suitably on the cortices. Due to the considerable stresses that they absorb, their upper part may develop clearance with the bone, this bringing about shearing movements even if the prosthesis is cemented in. In addition, they are heavy because they are solid.

It is an object of the improvements according to the present invention to remedy these drawbacks and to provide a prosthesis of which the femoral pin has a transverse elasticity which enables it to abut as well as possible against the cortices of the femur.

According to the invention, the femoral pin of the prosthesis is composed of a plurality of funicular elements issuing from the hilt member.

The conventional solid pin is thus replaced by a series of funicular elements or strands which come into contact with the cortices and pass through the spongy matter to obtain an excellent distribution of the strains to which the prosthesis is subjected. The strands are in slightly spaced apart relationship to allow the bone, in the course of reconstitution, to grow in the interstices therebetween.

The invention will be more readily understood on reading the following description with reference to the accompanying drawings, in which:

FIG. 1 is a view in elevation of the femoral pin of a prosthesis according to the invention.

FIGS. 2 and 3 are sections thereof along II—II and III—III (FIG. 1).

FIG. 4 is a side view of the femoral prosthesis shown in FIG. 1.

Referring now to the drawings, FIG. 1 shows the femoral pin of a hip prosthesis according to the invention, comprising a pin 1 surmounted by a pivot 2 which rises perpendicularly with respect to a hilt member 3, as is well known in the art.

The femoral pin 1 shown in FIGS. 1 to 4 comprises a plurality of funicular elements or strands issuing from the hilt member 3. The outer strands 4, 5, 6, 7 represent the outer edges (FIGS. 2 and 3) of a curved contour, said strands being welded together at 8 at their free end.

Between the four strands forming edges, a plurality of other strands have been provided in the example shown, certain pairs of which are of identical length. For example, between strands 5 and 6 there is disposed a pair of strands 9, 10 which extend almost to the level of join 8, joining at 11.

As shown in the Figures, three other pairs of strands 12, 13, 14 are provided, having progressively shorter lengths. Like the others, these three pairs of strands are connected at their free end.

Separate strands 15, 16 and 17 are placed along the central axis of the section determined by the strands 4, 5, 6 and 7, two other strands of the same type, 18 and 19, are disposed in a plane perpendicular to the one passing through the other three and in the vicinity of strands 4 and 7.

A femoral pin for a hip prosthesis has thus been produced which may be very long so as to be well adapted to the medullary cavity with a view to better distributing the stresses that it receives. As a few tenths of millimeters separate the different strands to provide interstices, the latter are filled by the bone when it grows again, with the result that the connection of the femoral pin with the femur is particularly solid. The strands may be rough, this further improving the union of the bone and the prosthesis.

The fixing of the strands to the hilt member 3 is of particular importance, as they must conserve their dimensions on the one hand and, on the other hand, their hammer-hardening must be maintained constant over the whole of their length with a view to avoiding zones of rupture by fatigue. Consequently, they may either be riveted, or welded by electron bombardment, or they may be associated with the hilt member by cold welding. In this latter case, the end of each strand is threaded, the pitch of which is different from that of a hole made in the hilt member to receive their strand. The fact of screwing the strand causes a type of jamming which assures a good join. Of course, in this case, each strand is independent from the others so that it may rotate on itself.

A femoral pin for a hip prosthesis has thus been produced which is particularly well adapted to the medullary cavity and which allows the possibility of considerable bone growth. Of course, such a prosthesis may be fixed to the medullary cavity by means of a conventional plastic seal which reinforces the anchoring effect ensured by the above-mentioned bone growth; a reinforced assembly is then obtained whose structure may be compared to that of reinforced concrete.

The description given hereinabove has, of course, been given only be way of example and it in no way limits the field of the invention, the replacement of details described by any other equivalents not departing from the scope thereof. In particular, the strands may be twisted or interlaced, whilst being independent, or connected differently to one another.

What is claimed is:

1. In a hip prosthesis of the type having a hilt member for engaging the end of a femur and having a pivot member extending from the hilt member in one direction and having a pin member extending longitudinally in the other direction from the hilt member along a curved axis with a tapered contour shaped to fit into the medullary cavity of the femur, the improvement wherein the pin member comprises:
   (a) a multiplicity of funicular strands grouped together to form the composite contour of said pin member, the strands having first ends fixed to said hilt member, and the strands having graduated lengths and being grouped according to lengths and having second ends connected together; and
   (b) the longest strands forming the outer contour of the pin member, and the shorter strands having their second ends terminating at multiple points inside the pin member, which points are located progressively closer to the hilt member within said tapered contour.

2. In a prosthesis as claimed in claim 1, said tapered contour having a substantially rectangular cross-section defined by four of the longest strands, and the four strands having their second ends joined to form the smaller end of the tapered contour located remotely from the hilt member.

3. The prosthesis as claimed in claim 2, wherein the strands are welded at their ends.

4. The prosthesis as claimed in claim 1, wherein the strands are hardened.

* * * * *